United States Patent [19]

Inoue et al.

[11] Patent Number: 4,717,387
[45] Date of Patent: Jan. 5, 1988

[54] CATHETER

[75] Inventors: Kiyoshi Inoue, Urawa; Keiichi Kuwaki, Tokyo; Koichi Tsuno, Osaka, all of Japan

[73] Assignee: Sumitomo Electric Industries Ltd., Japan

[21] Appl. No.: 878,133

[22] Filed: Jun. 25, 1986

Related U.S. Application Data

[62] Division of Ser. No. 592,719, Mar. 23, 1984, Pat. No. 4,619,247.

[51] Int. Cl.⁴ ............... A61M 5/325; A61M 35/00
[52] U.S. Cl. ........................... 604/264; 604/265; 604/2
[58] Field of Search ............ 604/1, 2, 11, 264, 265, 604/268, 280, 282, 283, 104; 401/196, 203, 207; 128/343

[56] References Cited

U.S. PATENT DOCUMENTS

| | | | |
|---|---|---|---|
| 1,687,472 | 10/1928 | Dorman et al. | 604/1 |
| 2,218,738 | 10/1940 | Boysen | 604/1 |
| 2,759,209 | 8/1956 | Ferrari | 401/203 |
| 3,369,543 | 2/1968 | Ronco | 604/2 |
| 3,614,245 | 10/1971 | Schwartzman | 604/2 |
| 3,938,898 | 2/1976 | Reitknecht | 401/207 |
| 3,965,909 | 6/1976 | Waddell et al. | 604/269 |
| 4,165,942 | 8/1979 | Johansson | 401/203 |
| 4,183,328 | 1/1980 | Lawrence | 604/2 |
| 4,480,940 | 11/1984 | Woodruff | 401/207 |
| 4,578,055 | 3/1986 | Fischer | 604/2 |

Primary Examiner—C. Fred Rosenbaum
Assistant Examiner—Gene B. Kartchner
Attorney, Agent, or Firm—Harness, Dickey & Pierce

[57] ABSTRACT

A catheter or fiberscope for the inspection of an intracardiac area or the like is proposed which has a flexible tube and a balloon mounted on its end. The flexible tube is divided into four passageways, i.e. two fluid passageways and an illumination light transmission line and an image transmission line. A flush of a physiological saline solution is spouted from one fluid passageway outside of the balloon to form a visual field without interfering natural movement of the area to be inspected. A catheter for dissolving a thrombus is also proposed which has a porous tube, instead of a balloon, at its end portion.

6 Claims, 13 Drawing Figures

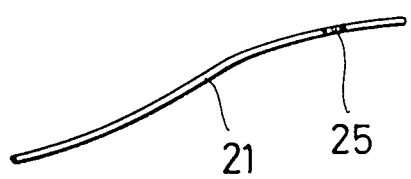
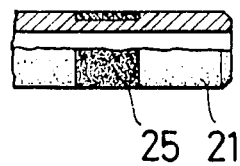
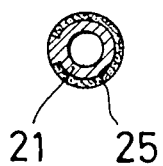
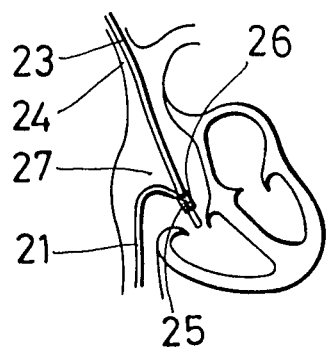
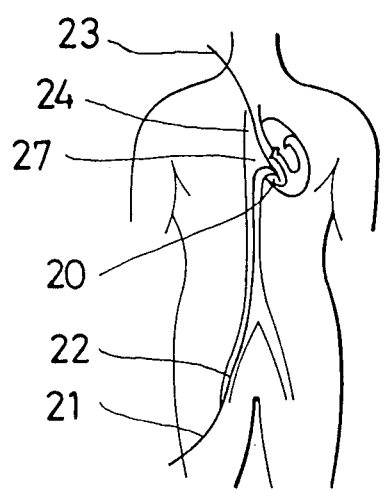
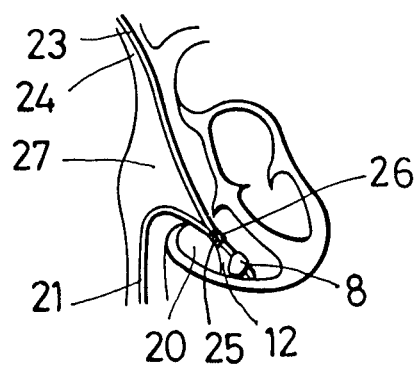

CATHETER

This is a division of application Ser. No. 592,719, filed Mar. 23, 1984 now U.S. Pat. No. 4,619,247.

The present invention relates to a catheter or fiberscope which is inserted into a heart, blood vessel or ureter for injection or withdrawal of fluids or inspection or observation of the interior.

It is known, with a view to removing the blood from the area to be inspected so as to form a transparent visual field, to feed a physiological saline solution or carbonic acid gas from a syringe to a transparent balloon mounted on the end of a catheter or fiberscope to inflate the balloon, or to feed a physiological saline solution from a syringe to an opening provided at the end of the fiberscope to spout a flush of the physiological saline solution therefrom.

However, the latter method requires that a large quantity of physiological saline solution be rapidly injected to secure a visual field in case a wide area such as an intracardiac area is to be inspected. A disadvantage derived from this is that the passageway for the physiological saline solution and thus the catheter or fiberscope must have a large outside diameter.

On the other hand, the former method makes it difficult to accurately observe and measure an object because this system is devoid of a mechanism for securely holding the inflated balloon at the end of the fiberscope and consequently the balloon shifts out of position when it is pressed against a cardiac inner surface, etc. The balloon might break if it is pressed too hard or when the edge portion at the end of the fiberscope touches the balloon. Other disadvantages are that because the balloon is pressed against the object to be inspected, the object is hindered from its natural movement during observation and that because the surface of the balloon is kept in touch with the blood, a thrombus is apt to be formed on the surface of the balloon.

It is an object of the present invention to provide a catheter or fiberscope by which the object to be inspected is not hindered from its natural movement for exact observation.

It is another object of the present invention to provide a catheter or fiberscope which can avoid thrombogenesis.

According to the present invention, a passageway for transmitting the light for illumination, a passageway for transmitting an image and passageways for feeding a transparent fluid run parallel with each other in a flexible tube. An inflatable transparent balloon for building up a visual field is provided at the end of the passageway for feeding a transparent fluid so as to communicate therewith. This balloon is adapted to cover the ends of the passageway for transmitting the illumination light and the passageway for transmitting an image. An opening for spouting a flush of a transparent liquid is provided so that the surface of the balloon at the end of the fiberscope can be washed. In order to inspect an intracardiac surface, the balloon is not directly pressed against the object but a comparatively small quantity of a transparent fluid is spouted from the above-described opening into the space between the object and the balloon so as to wash the surface of the balloon and build up a transparent visual field at the end of the fiberscope.

This arrangement has advantages that the passageway for feeding a transparent liquid has a considerably smaller outside diameter as compared with the conventional fiberscope, that the object to be inspected is not hindered from its natural movement, that the visual field is broadened, that undue shift or damage of the balloon is prevented, and that the formation of thrombus on the surface of the balloon can be avoided.

Other and further details of the present invention are hereinafter described with reference to the accompanying drawings, in which:

FIG. 4 is a schematic view of a catheter in accordance with the present invention;

FIGS. 5A and 5B are longitudinal and transverse sections, respectively, of an end portion thereof;

FIG. 6 is a view showing how an affected part is inspected;

FIGS. 7A and 7B are enlarged views of the cardiac area of the patient's body shown in FIG. 6;

Figure 1:
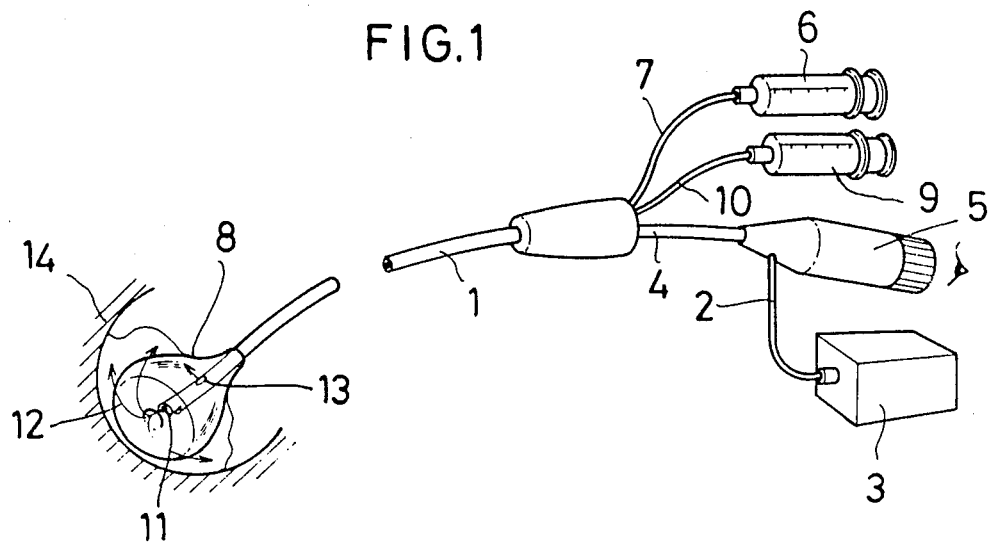
FIG. 1 is a schematic illustration of a fiberscope in accordance with the present invention.
Figure 2:
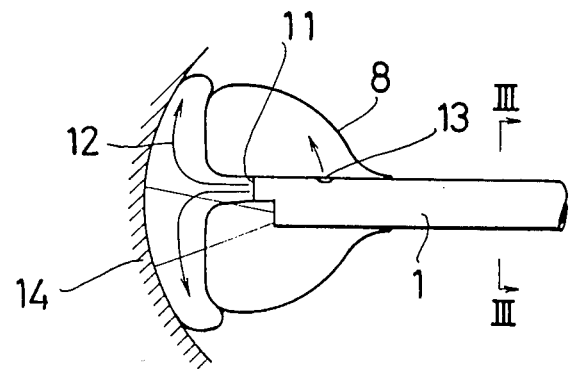
FIG. 2 is an enlarged side view of an end portion of the fiberscope shown in FIG. 1.
Figure 3:
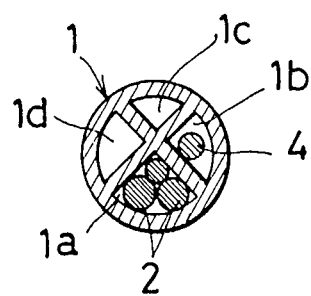
FIG. 3 is a sectional view taken along line III—III of FIG. 2.
Figure 8:
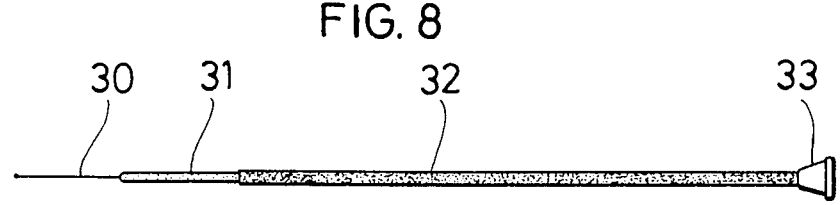
FIG. 8 is a side view of another embodiment in accordance with the present invention.

Referring now to FIGS. 1 to 3 showing an embodiment, a slender flexible tube 1 is adapted for insertion into a heart, etc. Its interior is divided into four passageways 1a, 1b, 1c and 1d. (FIG. 3) The passageway 1a accommodates optical fibers 2 through which the light for illumination is transmitted from a light source 3 to the area to be inspected. The passageway 1b accommodates an image fiber 4 which forms an image transmission line, has a lens at its end to focus the image from the object and sends to an image-receiving adapter 5. The passageway 1c serves to feed a transparent fluid such as a physiological saline solution or carbonic acid gas from a syringe 6 through a pipe 7 to a transparent balloon 8 mounted on the end of the fiberscope to inflate the balloon. The passageway 1d serves to feed a transparent liquid such as a physiological saline solution from a syringe 9 through a pipe 10 to an opening 11 provided at the end of the fiberscope so that a flush 12 of the physiological saline solution will be spouted therefrom.

The flexible tube 1 may be made of such a material as polyvinyl chloride and ethylene vinyl acetate and polyurethane by the extraction process. The balloon 8 is adapted to surround the end portion of the fiberscope so as to cover the ends of the optical fiber 2 and the front of the lens provided at the end of the image fiber 4. An exhaust port 13 through which a transparent fluid is spouted to inflate the balloon 8 is provided in the side wall of the flexible tube 1. If a comparatively flat area such as a cardiac inner surface 14 is to be inspected, it is preferable to adjust the wall thickness of the balloon 8 so that when the balloon is inflated, its front surface will be made flat in agreement with the shape of the object to be inspected, as shown in FIG. 2.

The opening 11 is provided at such a position that the surface of the balloon 8, e.g. in the center of the annular balloon. When the balloon is inflated, the opening 11 is adapted to form a flush 12 of the physiological saline solution in front of the balloon.

In order to build up a visual field in the above-described fiberscope, the balloon 8 is inflated as shown in FIG. 2 to ensure a visual field in the blood and is put close to the area to be inspected. Then the physiological saline solution is spouted from the opening 11 so as to form a comparatively thin layer of a flush 12 of the physiological saline solution between the area to be inspected and the front surface of the balloon 8 and thereby keep them out of contact with each other while building up a transparent visual field in front of the image fiber and the light guide.

Thus the balloon 8 is not pressed against the object to be inspected and yet a visual field is ensured. Therefore, the danger of the balloon shifting or breaking at the end of the fiberscope is substantially reduced. Since the balloon is not pressed against the object, the object is not hindered from its natural movement but exposes itself for exact observation. Thrombogenesis on the surface of the balloon can be avoided, because the flush 12 of the physiological saline solution is formed to wash the surface of the balloon. A considerably smaller quantity of a physiological saline solution is enough for the formation of the flush. Therefore, the passageway 1d may have a small sectional area so as to allow the fiberscope to have a comparatively small outside diameter.

In the above-described embodiment, the optical fibers are used as the light guides for transmitting the light for illumination. However, the light guides may be a transparent tube made of plastic such as polymethyl methacrylate, polystyrene or polycarbonate.

The above-described embodiment has been described particularly to a fiberscope for use in intracardiac inspection. However, the fiberscope in accordance with the present invention can also be used for the inspection of other organs such as the interior of a blood vessel and for the inspection of the inner surface of a tank or a pipe containing a liquid having a high optical density such as crude oil or chemicals.

Referring now to FIG. 6, the inspection of the interior of a right ventricle will be described for an example. A catheter 21 for spouting a flush of a physiological saline solution for removing the blood is inserted into the right ventricle 20 through a femoral vein 22. A fiberscope catheter 23, which accommodates a light guide for transmitting the light for illumination and an image fiber for transmitting an image and is provided with a transparent balloon 8 for removing the blood, is also inserted into the right ventricle 20 through an ascending vena cava 24. This method is effective when the insertion of two catheters through a single vein is a severe burden on a patient. In FIG. 7, the balloon 8 on the end of the fiberscope catheter 23 inserted into the right ventricle 20 is inflated. A flush 12 of a physiological saline solution is spouted from the catheter 21 so as to wash the surface of the balloon 8. The flush serves to broaden the visual field and prevent thrombogenesis on the surface of the balloon by removing the blood from the space between the balloon and the inner wall.

Referring now to FIGS. 4, 5 and 7, annular magnets 25 and 26 are fitted on the end of the catheters 21 and 23, respectively, so that both end portions will be put together by these magnets when they come close to each other in the proximity of a right atrium 27 as shown in FIG. 7A. Then the catheters 21 and 23 are further inserted until they are suitably positioned for inspection in the right ventricle 20 as shown in FIG. 7B.

This arrangement has advantages that the balloon 8 can be suitably positioned relative to the flush 12, that the visual field can be stabilized without the fear of having the balloon blown off by the flush 12, and that a plurality of catheters can be easily put together in the proximity of a target region.

The above-described arrangement is not only applicable to fiberscope but also effective when a plurality of catheters are destined for a single target region through separate paths.

Figure 9:
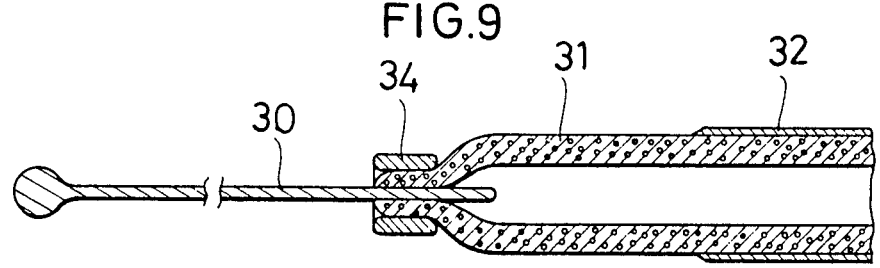
FIG. 9 is an enlarged view of an end portion thereof.

Referring now to FIGS. 8 to 11, the second embodiment of the present invention includes a guide wire 30, a chemical delivery tube 31, a covering 32, and a coupler 33 for coupling a syringe. As shown in FIG. 9 the chemical delivery tube 31 is a porous tube made of a material such as ethylene tetrafluoride resin. To the end of the chemical delivery tube 31, the guide wire 30 is secured by means of a neck ring 34. Except for the end portion extending for about 10 to 20 mm, the chemical delivery tube 31 is covered with the covering 32 made of a material such as fluororubber and silicicrubber. The covering 32 should be capable of resisting the pressure for injecting a thrombus dissolving agent so that the agent will be delivered only from the uncovered end of the chemical delivery tube 31. The covered portion has an outside diameter of about 1 mm.

Figure 10:
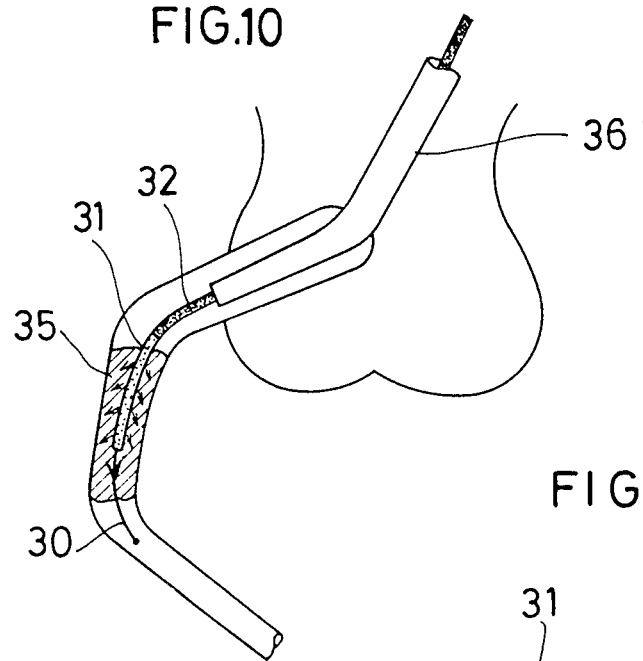
FIG. 10 is a view showing how it is used.
Figure 11:
FIG. 11 is a side view of an end portion of still another embodiment of the present invention.

In order to dissolve a thrombus 35, the catheter in accordance with this embodiment is passed through a cardiac catheter 36 as shown in FIG. 10. Firstly the guide wire 30 passes through the thrombus 35. The catheter in accordance with this embodiment is further advanced until the uncovered end of the chemical delivery tube 31 is inserted into the thrombus 35. Then the thrombus dissolving agent is injected through the coupler 33 and delivered from the uncovered end of the chemical delivery tube 31. Dissolution occurs over a wide range of the thrombus. As shown in FIG. 11, the guide wire 30 may be omitted with the uncovered end of the chemical delivery tube 31 tapered.

The above-described embodiment has the advantages that since dissolution occurs over a wide range of the thrombus, high efficiency in medical treatment is provided, that the danger of undissolved thrombus getting off the wall of a blood vessel and blocking the blood vessel is minimized, and that the catheter in accordance with this embodiment is antithrombotic because the chemical delivery tube is made of a fluorocarbon resin.

What are claimed are:

1. A catheter for insertion into a living body comprising a flexible tube having a fluid passageway for a first fluid, means at the rear end portion of said tube for providing a connection to means for admitting a first fluid to said fluid passageway and means disposed at a front end portion of said flexible tube for allowing said first fluid fed through said fluid passageway from said rear end portion to eject into the living body to directions other than the axial direction as well as the axial direction, said flexible tube comprising a porous tube covered with a pressure-resistant covering except for end portion thereof, said means at the front end comprising the exposed end portion of said porous tube.

2. The catheter as claimed in claim 1, wherein said first fluid is a thrombus dissolving agent.

3. The catheter as claimed in claim 1, wherein said porous tube is made of fluoroethylene resin.

4. The catheter as claimed in claim 1, wherein said pressure-resistant covering is made of fluororubber or silicicrubber.

5. The catheter comprising a flexible tube having a fluid passageway for a first fluid, and means disposed at a front end portion of said flexible tube for allowing said first fluid fed through said fluid passageway to eject to directions other than the axial direction as well as the axial direction, said flexible tube comprising a porous tube covered with a pressure-resistant covering except for end portion thereof, said means at the front end comprising the exposed end portion of said porous tube, and a guide wire having its rear end inserted into said front end of said porous tube and secured thereto so as to protrude therefrom.

6. The catheter as claimed in claim 5, wherein said guide wire has a round end.

* * * * *